United States Patent [19]

Guo

[11] Patent Number: 4,818,537

[45] Date of Patent: Apr. 4, 1989

[54] LIPOSOME COMPOSITION FOR TREATING DRY EYE

[75] Inventor: Luke S. S. Guo, Lafayette, Calif.

[73] Assignee: Liposome Technology, Inc., Menlo Park, Calif.

[21] Appl. No.: 910,008

[22] Filed: Oct. 21, 1986

[51] Int. Cl.[4] .......................... A61F 2/00; A61K 9/66; B01J 13/02

[52] U.S. Cl. ........................ 424/427; 424/1.1; 424/450; 428/402.2; 436/829; 514/915

[58] Field of Search ............... 428/402.2; 424/427, 424/450; 514/915; 436/829

[56] References Cited

U.S. PATENT DOCUMENTS

| | | | |
|---|---|---|---|
| 4,201,767 | 5/1980 | Fullerton et al. | 424/450 X |
| 4,229,360 | 10/1980 | Schneider et al. | 424/450 X |
| 4,241,046 | 12/1980 | Papahadjopoulos et al. | 424/450 X |
| 4,350,676 | 9/1982 | Laties et al. | 424/9 X |
| 4,476,140 | 10/1984 | Sears et al. | 514/913 X |
| 4,565,696 | 1/1986 | Heath et al. | 514/2 X |
| 4,670,185 | 6/1987 | Fujiwara et al. | 264/4.1 X |

OTHER PUBLICATIONS

Helene E. Schaeffer and David L. Krohn. Liposomes In Topical Drug Delivery. Invest. Ophthalmol. Vix. Sci, Feb. 1982 pp. 220–227.

Primary Examiner—Richard D. Lovering

[57] ABSTRACT

A liposome composition useful in the treatment of dry eye. The composition includes an aqueous suspension of liposomes whose lipid composition preferably includes about 70–85 mole percent of hydrogenated phosphatidylcholine, and 15–30 mole percent of benzyldimethylstearylammonium chloride. The suspension is stable on storage at room temperature for several months.

13 Claims, 2 Drawing Sheets

LIPOSOME COMPOSITION FOR TREATING DRY EYE

FIELD OF THE INVENTION

This invention relates to a composition and method for treating dry eye.

REFERENCES

Lawrence, D. J., et al, Ann NY Acad Sci 106:646 (1963).
Lemp, M. A., Int Ophthalmol Clin 13:185 (1973).
Maurice, D., et al Toxicology Lett, (1986) in press.
Sjögren, H., et al, Surv Ophthalmol 16:145 (1971).
Szoka, F., Jr., et al, Ann Rev Biophys Bioeng 9:467 (1890).

BACKGROUND

Dry eye is an ophthalmic condition characterized by a discontinuous tear film of the ocular surface. The condition has a number of distinct etiologies, including poor water-secretion by the lacrimal gland (Sjogren), poor mucin secretion by the goblet cells (Lemp), vitamin A deficiency (Lawrence), and alteration of film-forming lipids as a result of chronic bletharitis.

Dry eye is usually treated by applying a slightly viscous polymer solution in drop form to the eye, to provide temporary wetting before the solution evaporates or is wiped away by blinking. Since the polymer solutions tend to be cleared from the eye rather quickly, frequent dosing may be required.

The usual dry eye formulation is a liquid which is intended to be stored at room temperature. For this reason, it is desirable that the product be stable on storage at room temperature over a several-month period. For polymer solutions of the type just described, the principal storage problem is bacterial growth, which can be controlled by the presence of a bacteriostatic compound. One bacteriostatic compound which has been widely used is benzalkonium chloride, at a solution concentration of about 0.01%. Although generally safe for ophthalmic use, the compound has been found to cause occasional eye irritation.

The inventors have previously proposed, in co-owned patent application for "Ophthalmic Liposomes", Ser. No. 890,817 filed June 19, 1986, the use of liposome suspensions for treating dry eye. This method of treatment provides several potential advantages over prior art treatment involving polymer solutions. Liposomes, when bound to the ocular surface, would provide a matrix for holding encapsulated and bound aqueous fluid, and thus could provide effective wetting as long as the liposomes are retained on the ocular surface. The liposomes can also provide muco-mimetic properties for forming a stable tear film on the eye. According to the earlier-described invention, and also to the invention disclosed herein, the liposomes can be formulated for retention on the ocular surface for up to several hours, and thus the need for frequent dosing is avoided. Further, the liposomes can be formulated to supply film-forming lipids and/or vitamin A which may be lacking in the patient receiving the treatment.

Although liposomes offer the potential for improved dry eye treatment, there are several challenges in the design of an effective dry eye formulation. One is that the product be stable for periods of up to several months. It is well-known that liposomes undergo a variety of lipid oxidation/peroxidation and hydrolysis reactions, even when stored at refrigerator temperature for several months. Another problem is achieving good optical clarity in the formulation, so that the liposomes do not impair or cloud vision. Finally, the liposome suspension must be compatible with an acceptable bacteriostatic agent.

SUMMARY OF THE INVENTION

It is one general object of the invention to provide an improved liposome composition and method for the treatment of dry eye.

It is a more specific object of the invention to provide such a composition which is (a) stable on storage for several months at room temperature, (b) has good optical clarity, and (c) is compatible with a suitable bacteriostatic agent. According to another aspect of the invention, the formulation also has reduced eye irritant properties.

Still another object of the invention is to provide such a liposome formulation which can be prepared in sterile form by relatively simple processing methods.

Providing a dry eye formulation having reduced tendency for eye irritation is yet another object of the invention.

The composition of the invention includes an aqueous suspension of liposomes whose lipid composition contains substantially saturated neutral vesicle-forming lipids, and between 10–40 mole percent of a quaternary benzyl amine having an aliphatic hydrocarbon chain of at least 12 carbon atoms. The aqueous medium is buffered to a preferred pH of between about 6.2 and 6.8, and may contain a bacteriostatic agent as well as a calcium-ion chelator, which acts to limit phospholipid hydrolysis, and further acts as a bacteriostatic agent. The liposomes composition may further include vitamin A and/or film forming lipids, such as long-chain fatty alcohols and cholesterol esters.

In a preferred embodiment, the liposomes are composed of between about 70–85 mole percent hydrogenated phosphatidylcholine (HPC) and between about 15–30 mole percent of benzyldimethylstearylammonium chloride (BDSA), and are present in the suspension at about 0.02 and 0.04 weight percent of the total composition. A preferred bacteriostatic agent is benzalkonium chloride, at a concentration of about 0.01 weight percent or less. This agent has reduced eye irritancy in the presence of liposomes.

The invention also includes a method of treating dry eye which includes the steps of (a) providing an aqueous suspension of liposomes formulated for enhanced retention on the ocular surface, and (b) applying the suspension to the ocular surface in an amount sufficient to form an aqueous liposome matrix coating the surface. The suspension has the characteristics of the above liposome composition.

These and other objects and features of the invention will become more apparent when the following detailed description of the invention is read in conjunction with the accompanying drawings.

DETAILED DESCRIPTION OF THE INVENTION

I. Preparation of the Liposome Composition

A. Components

1. Vesicle-Forming Lipids

Figure 1:
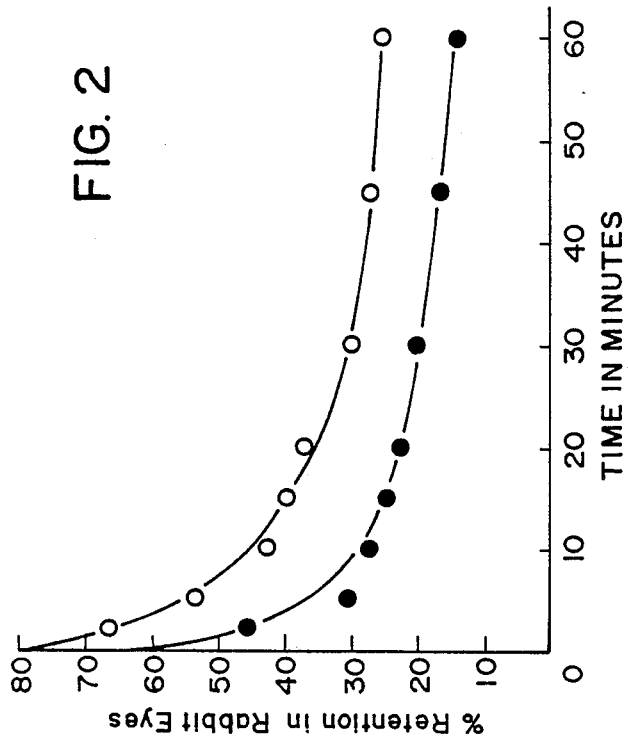
FIG. 1 shows the retention at an ocular tissue of SUVs prepared with hydrogenated phosphatidylcholine (HPC) alone (open circles) or SUVs with benzyldimethylstearylammonium chloride (BDSA) and hydrogenated PC (HPC), at a ratio of 4:1 HPC:BDSA (closed circles)

The liposomes of the composition can be formed from a variety of vesicle-forming lipids, which include dialiphatic chain lipids, such as phospholipids, diglycerides, and dialiphatic glycolipids, and cholesterol and derivatives thereof. The lipid components are present in an amount between about 60–90 of the total lipid components in the liposomes, the remainder being charged surface components described in the section below.

As defined herein, "phospholipids" include phosphatidic acid (PA) and phosphatidyl glycerol (PG), phosphatidylcholine (PC), phosphatidylethanolamine (PE), phosphatidylinositol (PI), phosphatidylserine (PS), plasmalogens, and sphingomyelin (SM). The term "cholesterol" is intended to encompass cholesterol derivatives such as: (3-hydroxy-5,6-cholestene) and related analogs, such as 3-amino-5,6-cholestene and 5,6-cholestene; cholestane, cholestanol and related analogs, such as 3-hydroxy-cholestane; and charged cholesterol derivatives such as cholesteryl β-alanine and cholesteryl hemisuccinate. The term "glycolipid" as used herein is intended to encompass lipids having two fatty acid chains, one of which is the hydrocarbon chain of sphingosine, and one or more sugar residues. Examples of glycolipids suitable for practice of the present invention include cerebrosides, galactocerebrosides, glucocerebrosides, sulfatides and sphingolipids with di- and trisaccharides as their polar head groups, i.e. di- and trihexosides.

In the dialiphatic chain lipids, such as phospholipids, which preferably make up the bulk of the vesicle-forming lipids, the aliphatic chains are preferably at least about 12 atoms in length, and optimally are between about 15 and 20 atoms long. The chains are also substantially saturated, by which is meant that each chain contains at most one unsaturated bond. The saturated aliphatic chains produce better lipid packing in the liposomes, which has been found to increase liposome binding to mucosal surfaces. More importantly, and according to experiments conducted in support of the present application, the saturated chains substantially eliminate lipid oxidative/peroxidative lipid damage on storage at room temperature over a several-month period. The lack of oxidative damage is observed even in the absence of lipophilic free-radical quenchers, such as α-tocopherol. However, such lipid protective agents may be added, if desired. Similarly, where steroid-type lipids are included in the liposomes, these are preferably saturated species, such as cholestanol and its analogues.

The lipids used to form the liposome compositions of the present invention may be either charged or neutral. Because it is desirable for enhanced retention of the composition that the overall liposome surface be positively charged, neutral or positively charged lipids are preferred. Negatively charged lipids may be incorporated within the liposomes, however, to the extent that the total negative charge on the lipids is relatively low compared with total positive charge which is imparted by the charged surface components discussed in the next section.

In a preferred formulation, 30–90 mole percent of the total lipids are phospholipids; still more preferably, 60–90 mole % of the total lipids are saturated, neutral phospholipids such as hydrogenated phosphatidylcholine (HPC). Up to 40 mole % of of the total lipids may represent a saturated cholesterol derivative. The liposome composition illustrated in Examples I and II below, and in several of the subsequent examples, the vesicle-forming lipids include 80 mole percent HPC.

The vesicle-forming lipids may further include vitamin A, which becomes entrapped predominantly in the liposomal bilayer region on liposome formation. The concentration of vitamin A is preferably between about 0.5 5.0 mole percent. The composition is useful in treating dry eye related to vitamin A deficiency.

For treating dry eye conditions which are related to lack of tear-forming lipids, the liposome composition may be further formulated to include minor amounts of fatty alcohols, fatty acids, and/or cholesterol esters, with the proviso that these minor lipid components (a) do not significantly reduce the binding affinity of the liposomes for mucosal tissue and (b) are substantially unsaturated, and (c) are not toxic or irritating to the eye. The first proscription limits the amount of negatively charged lipid which can be included in the liposomes, and also limits the amount of lipid which is disruptive of lipid packing in the liposome bilayer.

2. Charged surface components

The liposomes also contain 10–40 mole percent of a benzyl/aliphatic-chain amine which (a) is anchored in the liposome bilayer by virtue of its aliphatic chain and benzyl groups, and which is positively charged at a pH between about 6,2 and 6.8. The amines are preferably benzyl, dialkyl, aliphatic chain quaternary amines whose positive charge is independent of pH.

The aliphatic chain in the amine is at least 12 carbon atoms in length, and preferably between about 15 and 20 carbon atoms in length. In the quaternary amine compound, the remaining nitrogen linked groups are saturated alkyl substituents of less than about 5 carbon atoms. The benzyl group may be substituted with alkyl or other hydrophobic moieties. One preferred benzyl amine is benzyldimethylstearylammonium chloride (BDSA), and benzyldimethylaliphatic-chain amines in which the aliphatic chain is between about 15–20 atoms long.

Both the long chain aliphatic group and the benzyl group of the amine are hydrophobic moieties which anchor the molecule to the interior, hydrophobic area of the lipid bilayer. In contrast to amines of the prior art which were anchored to the bilayer by only one hydrophobic moiety, the composition of the present invention displays increased stability by virtue of the two hydrophobic, anchoring functionalities on the amine. The stability of one preferred liposome composition, which contains HPC and BDSA at a mole ratio of 4:1, is seen in Example VI and in FIG. 4, which shows differential scanning calorimetry thermograms for free HPC (upper trace), free BDSA (lower trace), and HPC/BDSA liposomes (middle trace). The liposome composition contains no detectable free BDSA.

That the added amine significantly enhances liposome retention to the ocular tissue is demonstrated in the studies reported in Example III, involving liposomes formed with PC and 20 mole percent BDSA. As seen in FIG. 1, addition of BDSA (solid circles in FIG. 1) produces a 3–4 fold enhancement in liposome retention to the eye, one hour after administration.

According to an important feature of the invention, the charged, amine-containing liposomes show little or no eye irritation in a variety of eye irritation tests (reported in Examples IX and X). In particular, BDSA appears to be significantly less irritating when associated with liposomes than when administered to the eye in free form.

3. Chelating agent

The composition may include a calcium-ion chelating agent which functions both to reduce lipid hydrolysis in the liposomes, and contribute to bacteriostatic action. The inhibition of lipid hydrolysis is due to inhibition of phospholipase $A_2$, which may be present in the suspension as a contaminant, and which requires calcium as a cofactor. The bacteriostatic action of the chelator is related to sequestering of metals in a non-utilizable form.

Examples of chelating agents which are useful in complexing each of these ions include ethylenediaminetetraacetic acid (EDTA), ethylenediaminetriacetic acid (ED3A) and diethylenetriaminepentaacetic (DTPA). The chelator is added in an amount greater than the calcium ion concentration in the suspension, and typically between about 25–50 μM.

4. Viscosity-Related Polymers

In order to further improve retention of the liposome composition on the ocular surface, a number of high molecular weight polymeric agents may be included in the aqueous dispersion. Suitable polymers include but are not limited to cellulosic polymers such as hydroxyethylcellulose, hydroxypropylcellulose, methylcellulose, vinylic polymers such as polyvinylpyrrolidone and polyvinylalcohol, and mixtures thereof.

The polymers act to enhance liposome retention on an ocular surface, presumably by increasing the viscosity of the aqueous suspension medium, and/or by forming linked liposome aggregates on the ocular surface. The enhanced retention of liposomes due to the addition of a polymer mixture of 0.8% hydroxymethylcellulose and 0.2% polyvinylalcohol is seen in Example IV and FIG. 2. Briefly, as seen in the figure, the polymer mixture increased ocular retention, after 1 hour, by 60–70 percent.

Although the polymers were found to cause liposome flocculation on storage, the flocculant could be readily dispersed by gentle shaking to form a slightly opaque suspension. The stability of the liposome/polymer suspension, in accelerated stability studies is reported in Example VIII.

5. Suspension pH and Buffer

Figure 5:
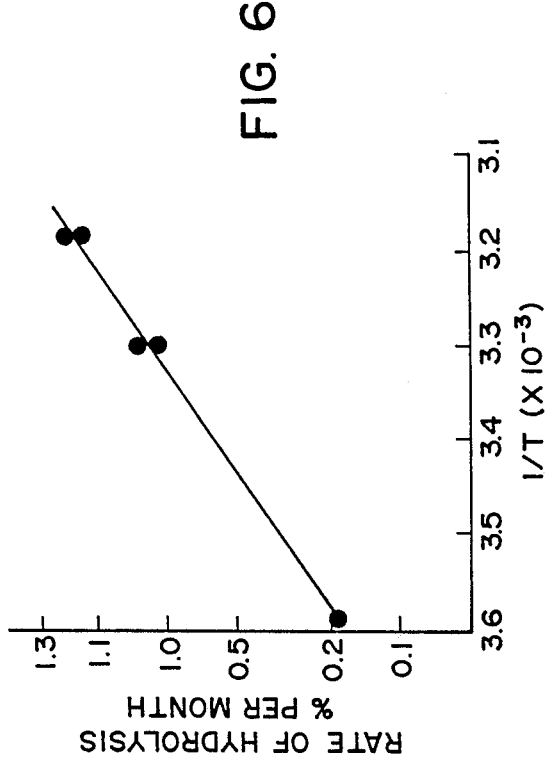
FIG. 5 shows of rate of hydrolysis of phospholipids in a suspension of HPC/BDSA SUVs containing polymers, when incubated at 70° C. at pH 6.0 (open triangles), pH 6.8 (closed triangles), pH 7.4 (open circles), and pH 8.0, closed circles.

Experiments conducted in support of the application, and reported in Example V, demonstrate that lipid hydrolysis of phospholipids is quite sensitive to suspension pH. The hydrolysis rates at four pH values between 6.0 and 8.0, over a five-day period at 70° C., are seen in FIG. 5. At pH 6.0, little hydrolysis is observed over the test period, and with increasing pH, increasing rates of hydrolysis occur. Studies reported in Example VIII indicate that the amount of hydrolysis observed after 4.5 months at 38° C., pH 6.86 is only about 12%, and that at pH 6.7, the rate was less. At room temperature, the extent of hydrolysis after 4.5 months, pH 6.86 was only about 6.7%.

Based on these results, an optimal pH of less than about 6.8, and preferably between 6.3 and 6.7 was selected. A 13 mM phosphate buffer gave good buffering capacity during the long-term storage.

6. Bacteriostatic agent

Figure 7:
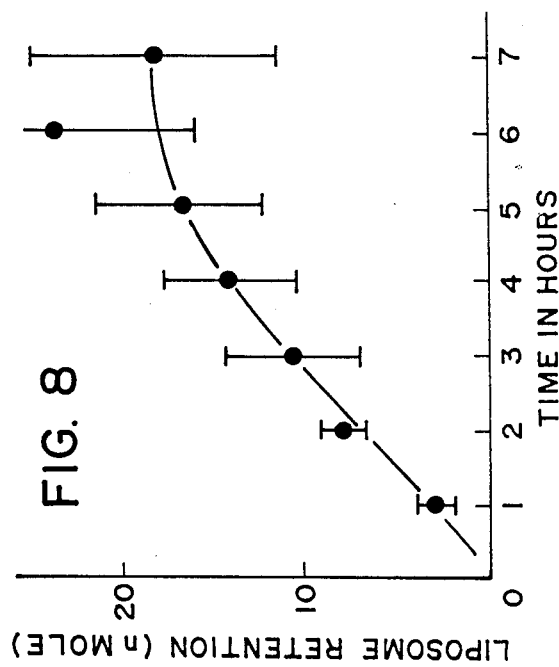
FIG. 7 plots the extent of corneal permeability of a fluorescence dye, at increasing concentrations of BDSA, when BDSA is in free (open circles) or liposomal (closed circles) form, and at increasing concentrations of benzalkonium chloride (BAC), also in free (open triangles) or liposomal (closed triangles) form.

The liposome composition preferably includes a bacteriostatic agent in addition to the calcium ion chelator included in the suspension. Studies conducted in support of the application indicate that BDSA contained in the liposomes was not an effective bacteriostatic agent, at the concentration tested (0.05% BDSA). In tests conducted with other bacteriostats, it was found that 0.01% benzalkonium chloride (BAC), at a concentration of 0.01%, gave good bacteriostatic effect. This compound is related to BDSA but contains aliphatic chains which are predominantly 12–14 carbon atoms long. Therefore the compound would be expected to have lower affinity for liposomes. However, some interaction between the compound and liposomes appears to occur, as evidenced by the reduced eye irritancy which is observed when the compound is formulated with liposomes (Example IX). The effect of liposomes in preventing eye irritation by both BDSA and BAC is seen in FIG. 7, showing that liposomes prevent the concentration dependent increases in irritation seen with both compounds in free form. One novel aspect of the invention, as indicated above, is this reduced eye irritation of BAC, without apparent loss of bacteriostatic activity.

B. Preparing the Liposome Composition

The liposome suspension of the invention can be prepared by standard methods for preparing and sizing liposomes. These include hydration of lipid films, solvent injection, reverse-phase evaporation, and other methods, such as those detailed in Szoka et al. Example I describes the preparation of reverse-phase evaporation vesicles (REVs) by the reverse-evaporation phase method described in U.S. Pat. No. 4,235,871. Example II describes the preparation of multilamellar vesicles (MLVs) by solvent hydration of a lipid film. In the later procedure, which is generally preferred, a mixture of liposome-forming lipids dissolved in a suitable solvent is evaporated in a vessel to form a thin film, which is then covered by an aqueous buffer solution. The lipid film hydrates to form MLVs, typically with sizes between about 0.1 to 10 microns.

Either the REV or MLV preparations can be further treated to produce a suspension of smaller, relatively homogeneous-size liposomes, in the 0.1–1.0 micron size range. Advantages of smaller, more homogeneous-size liposomes are: (1) less tendency to agglutinate, (2) higher density of liposome packing allowed at a mucosal tissue surface, and (3) greater optical clarity when applied to the eye. One effective sizing method involves extruding an aqueous suspension of the liposomes through a polycarbonate membrane having a selected uniform pore size, typically 0.2, 0.4, 0.6, 0.8 or 1 microns (Szoka et al). The pore size of the membrane corresponds roughly to the largest sizes of liposomes produced by extrusion through that membrane, particularly where the preparation is extruded two or more times through the same membrane. A more recent method involves extrusion through an asymmetric ceramic filter. The method is detailed in co-owned U.S. patent application for Liposome Extrusion Method, Ser. No. 829,710, filed Feb. 13, 1986, now U.S. Pat. No. 4,737,323.

Alternatively, the REV or MLV preparations can be treated to produce small unilamellar vesicles which are characterized by sizes in the 0.04–0.08 micron range. Because of the small particle sizes, SUV suspensions can be optically quite clear, and thus advantageous for ophthalmic applications. Another advantage of SUVs, as suggested above, is the greater packing density of liposomes on a mucosal surface which can be achieved with smaller liposome particles.

One preferred method for producing SUVs is by homogenizing an MLV preparation, using a conventional high pressure homogenizer of the type used commercially for milk homogenization. Here the MLV preparation is cycled through the homogenizer, with periodic sampling of particle sizes to determine when the MLVs have been substantially converted to SUVs. This method is illustrated in Example II, which describes the conversion of MLVs to SUVs with both moderate-pressure and high-pressure homogenization.

II. Method of Use

In the treatment of dry eye, a formulation as described above is applied to the ocular surface to increase fluidity, and, if necessary, to supply vitamin A and/or film-forming lipids to the ocular tissue. The composition is applied in an amount and at a frequency sufficient to increase the lubrication and moisture retention at the ocular surface.

Optimal Liposome Dose

Concentration of the liposomes present in the in the formulation may directly affect the efficacy of the product. The proposed liposome concentration of 0.4% (phospholipids, 0.362%; BDSA, 0.05%) is based on a theoretical calculation of the number of the liposomes available to the eye surface and results of rabbit eye retention studies, and eye irritancy measurements.

Calculations Based on Monolayer of Liposomes on the Ocular Surface.

Assuming the total ocular surface are of the human eye, including conjunctiva and cornea, to be about 20 $cm^2$, and the mean diameter of the small unilamellar liposomes to be 50 nm, it can be estimated that $1.0 \times 10^{12}$ vesicles are needed to cover a monolayer of liposomes on the ocular surface. Each 25 μl eye drop of 0.4% liposome formulation has about $3.7 \times 10^{12}$ vesicles. Therefore, each eye drop should provide approximately a 4-fold excess of vesicles to saturate a monolayer of liposomes on the eye surface From the foregoing, it can be appreciated how various objects and features of the invention are met. The invention provides a liquid dry eye composition which is stable on storage for several months at room temperature, by virtue of its lipid composition, chelator and bacteriostatic components, and the suspension pH. The product can be formulated with good optical clarity, relating both to small liposome size and good compatability between the liposomes and high-viscosity polymers.

These advantages are achieved in a charged liposome composition which has enhanced binding affinity for ocular tissue. In particular, the combination of charged surface amine groups on the liposomes and high viscosity polymers enhances liposome retention on the eye by as much as 3–4 fold over uncharged liposomes in the absence of polymer.

According to another advantage of the invention, the composition shows reduced eye irritancy due to the presence of bacteriostatic agent. This effect is presumably due to the ability of liposomes to sequester a certain proportion of the bacteriostatic agent in a form which is non-irritating, yet still capable of providing adequate bacteriostatic action.

Yet another advantage of the invention is the capability of supplying lipophilic agents, such as vitamin A or film-forming lipids, which are known to be deficient in some forms of dry eye.

The following examples illustrate methods for making and using the liposome composition of the invention, but are in no way intended to limit the scope of the invention.

Materials: Hydrogenated soy PC (HPC) and partially hydrogenated soy PC were obtained from American Lecithin Company (Atlanta, GA), and Asahi Chemical Industry (Japan), respectively. Benzyldimethylstearylammonium chloride was obtained from Aldrich Chemical Co. (Milwaukee, WI) and benzalkonium chloride (BAC), from Barnes-Hind, Inc (Sunnyvale, CA).

EXAMPLE I

Preparation of Sized REVs

This example describes the preparation of sized reverse phase evaporation vesicles (REVs) containing 80 mole percent hydrogenated soy phosphatidylcholine (HPC) and 20 mole percent benzyldimethylstearylammonium chloride (BDSA). The fatty acid composition of HPC is as follows: 16:0 (7.7%); 18:0 (85.3); 18:2 (0.9%); 18:2 (0.7%); and 20:0/20:1 (0.8%). Thus the total percentage of unsaturated fatty acyl moieties is less than 2.5%.

A total of 80 mg of the above lipid composition was dissolved in 10 ml of diethyl ether. An aqueous buffer containing 13 mM phosphate, 140 mM NaCl, pH 6.7 was added to the organic solvent to a final volume of 13 ml, and the mixture was emulsified by sonication for 1 minute, maintaining the temperature of the solution at or below room temperature. The ether solvent was removed under reduced pressure at room temperature, and the resulting gel was taken up in 10 ml of the above buffer, and shaken vigorously. The resulting REV suspension had particle sizes, as determined by microscopic examination, of between about 0.1 to 20 microns, and the was composed predominatly of relatively large (greater than 1 micron) vesicles having one or only a few bilayer lamellae.

The REVs were sized by several passes through a 0.2 micron polycarbonate filter, obtained from Biorad (Richmond, CA). Extrusion pressure was about 50 psi.

The extruded vesicles were predominantly 0.2 microns and less in size, and could be readily filtered through a 0.45 micron depth filter, for sterilization.

EXAMPLE II

Preparation of SUVs

This example describes the preparation of small unilamellar vesicles (SUVs), by homogenization of multilamellar vesicles (MLVs).

A total of 7.2 g of hydrogenated soy PC (80 mole %) and BDSA (20 mole %) was dissolved in 500 ml tertiary butanol. The dissolved lipid/amine composition was freeze dried, then 1 liter of saline-buffer containing 13 mM phosphate, 140 mM NaCl, 0.02% EDTA, pH 7.4, was added to the lipid film. The MLVs formed on gentle shaking for two hours at 60° C. had heterogeneous sizes between about 0.05 to 20 microns, and a predominance of multilayered structures.

About 1 liter of the MLV suspension from above was cycled through a Gaulin Homogenizer, Model 15 M, (Everett, MA), at about 9000 psi, the optimum recommended operating pressure. Aliquots were withdrawn after numbers of cycles for analysis of particle size by dynamic laser particle sizing. The distribution of particle sizes was also examined by molecular sieve chromatography, using a 2% agarose gel (Bio-Gel A 40M) column. Profiles of lipid phosphorous eluting from the column reflect the transformation of large, multilamellar vesicles which are contained in the void volume, to small unilamellar vesicles which are included in the column and elute as a broad peak between about 0.08 and 0.04 microns.

As the lipid suspension was cycled through the homogenizer, the mean particle size of the vesicles progressively decreased. Based on the column elution profiles, about 60%, 75%, 87%, and 90% of the MLVs were converted to SUVs (less than about 0.06 microns) after 10, 20, 30, and 50 passages, respectively. The final preparation showed good optical clarity.

When the same MLV suspension was homogenized in a very-high pressure homogenizer (French Pressure Cell Homogenizer, Model J4-3338, SLM-Aminco, Urbana, IL), operated at a pressure of about 20,000 psi, smaller liposomes and better optical clarity were achieved. Column elution showed that only about 5% of the lipid vesicles were not completely converted from MLVs to SUVs.

EXAMPLE III

Ocular Retention-Effect of BDSA

SUVs containing 80 mole percent of egg PC, and 20 mole percent BDSA and control SUVs containing egg PC only were prepared as in Example II. Both preparations contained about $10^5$ counts per minute (CPMs) of $^{125}$I-PE per 100 nmole lipid. The final concentration of the SUVs in both preparations was about 10 umole lipids/ml.

In vivo ocular retention studies were performed in rabbit eyes using a scintillation probe technique. In each experiment, 10 μl of liposomes containing about 100 nmole lipids and $10^5$ cpm of $^{125}$I-labeled PE were applied to the rabbit eye. Retention was assessed with the gamma probe positioned over the eye. A constant distance between the probe and the eye of 2 cm was insured by fitting the probe into a plexiglas sleeve-holder. A ⅛ inch thick lead partition placed against the lacrimal-nasal region of the rabbit effectively blocked radioactive material which drained into the nasolacrimal region. Retention time was monitored over a period of 1 hour unless specified otherwise. From the chart recordings, peak height readings were obtained. Total radioactivity of each reading was calculated from a standard curve by in vitro measurements of standard dilutions of the radioactive liposomes. Percent retention was calculated based on counts per minute (CPM) of the original 10 μl sample.

The percent retention was measured at 2, 5, 10, 15, 30, 30, 45, and 60 minutes. Retention times of the two SUV preparations are shown in FIG. 1, where the BDSA SUVs are represented by solid circles, and the control SUVs, by open circles. All values represent the mean of four rabbit eye measurements. As seen from the figure, neutral SUVs (solid squares) are retained only to a 7% after 1 hour. The BDSA liposomes, by contrast, showed about 20% retention after 1 hour.

EXAMPLE IV

Ocular Retention-Effect of Polymers

SUVs containing 80 mole percent egg PC and 20 mole percent lysinyl phosphatidylethanolamine (lysinyl PE) were prepared as in Example II. Lysinyl PE is an amine-derivatized PE formed by coupling the free PE amine to the carboxyl group of lysine through an amide linkage, as detailed in the above-cited patent application for "Ophthalmic Liposomes". A portion of the SUV preparation was mixed with an equal volume of polymer solution containing 0.8% hydroxymethylcellulose and 0.2% polyvinylalcohol, and the remainder (control) was mixed with an equal volume of buffer solution.

Figure 2:
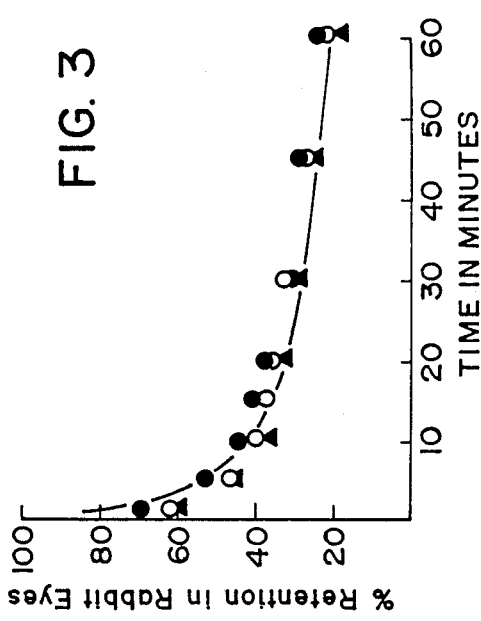
FIG. 2 shows the retention on an ocular tissue of HPC/BDSA SUVs formulated with (open circles) and without (closed circles) added polymers.

Both suspensions were tested for ocular retention as in Example III. The results obtained, representing an average of four animals for each time point, are shown in FIG. 2, where the polymer-containing SUVs are represented by open circles, and the non-polymer liposomes, by closed circles. As seen, the presence of polymers in the charged liposome suspension significantly enhanced retention over the 1 hour test period.

EXAMPLE V

Ocular Retention: Effect of Lipid Hydrolysis

The $pK_a$ of the carboxyl group in fatty acid is about 5. At neutral pH, free fatty acid produced by lipid hydrolysis (Example VII below) should be ionized and negatively charged. Eye retention of a positively charged liposomes may be diminished due to charge neutralization.

Figure 3:
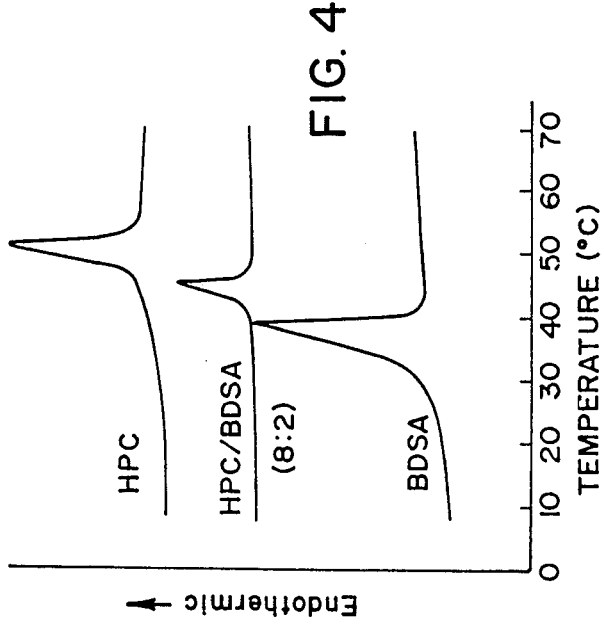
FIG. 3 shows the retention on an ocular tissue of HPC/BDSA SUVs formulated with 0 (closed circles), 10 (closed triangles), and 30 (open circles) mole percent of lysophosphatides and free fatty acids.

To determine the effect of partially hydrolyzed liposomes on eye retention, BDSA SUVs prepared as in Example II were formulated to contain 0, 10, or 30 mole % of free fatty acids and lysophospholipids. The SUV suspensions were evaluated in the rabbit eye model described in Example III and IV. Results of the experiment are shown in FIG. 3, which plot retention of SUVs containing 0 (solid circles), 10 (solid triangles), and 30 (open circles) mole percent free fatty acids. The data show that the retention of the liposomes over a period of one hour was not affected by the content of fatty acids and lysophospholipids.

EXAMPLE VI

Structural Stability of PC/BDSA SUVs

Figure 4:
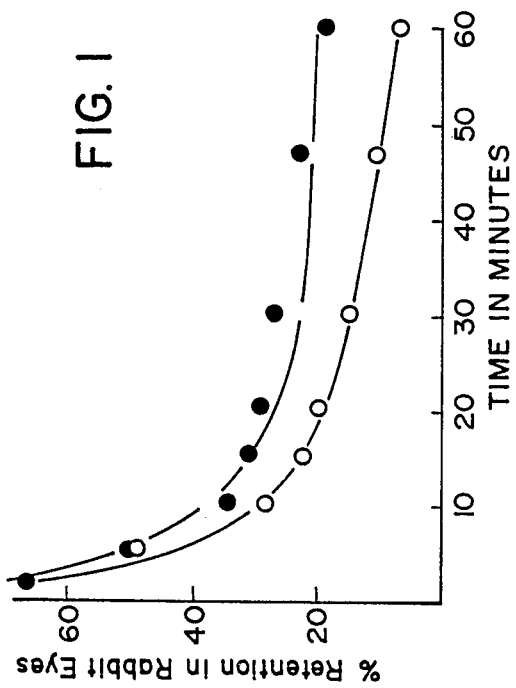
FIG. 4 shows differential scanning calorimetry thermograms for free HPC, free BDSA, and for HPC/BDSA SUVs.

The structural stability of the SUVs prepared as in Example II was evaluated by differential scanning calorimetry. As shown in FIG. 4, PC and BDSA alone each possess characteristic endothermic transitions at about 52° C. and 34° C., respectively. In the mixed liposome formulation, both parent transition peaks disappeared and showed a new endothermic transition at 45° C. Recycling the mixture between freezing (−34° C.) and heating (70° C.) did not change the phase transition profile. These results indicate the liposomes prepared with PC and BDSA at a molar ratio of about 4:1 were structurally stable, as no phase separation was observed at either high or low temperatures.

EXAMPLE VII

Lipid Hydrolysis in PC/BDSA SUVs

SUVs containing a 4:1 mole ratio of PC:BDSA were prepared as in Example II, in phosphate buffer adjusted to pH of 6.0, 6.8, 7.4, and 8.0. All four preparation were mixed with the polymer solution of Example IV. The four preparation were incubated at 70° C. for up to five days, with samples being taken at various times for determination of pH and lipid hydrolysis.

The pH of the medium was only slightly affected over the five day period for the three lowest pH suspensions. The pH 8 suspension fell to a final pH of about 7.5 over the five-day test period. Changes in pH were probably due to the production of free fatty acids and the formation of free acetic acid due to the presence of polyvinylacetate in the medium.

The extent of lipid hydrolysis, which results in the formation of lysophospholipids and free fatty acids, was determined as in Example VIII below. The results are shown in FIG. 5, where open triangle represent hydrolysis at pH 6.0; closed triangles, pH 6.8; open circles, pH 7.4; and closed circles, pH 8.0. As seen, the extent of hydrolysis is very sensitive to pH within the pH range tested.

Two SUV suspensions prepared in 13 mM and 26 mM phosphate buffer at pH 6.7 were tested for buffering capacity, using a back titration technique. Both buffers were adequate in preventing a significant pH drop (greater than 0.2 pH units) when over 70% of the lipids had been hydrolysed.

EXAMPLE VIII

Accelerated Stability Studies

A. Four month study at 38° C.

Two SUV suspensions, prepared as in Example II, were formulated were adjusted to pH 6.86 or a more optimal pH of 6.70. Both formulations were composed of HPC/BDSA liposomes and the Example IV polymers without additional preservative. Samples were kept in capped polyethylene tubes under sterile conditions at 4°, 30°, and 38° C. Because lipid hydrolysis appeared to be a major stability concern, hydrolysis of phospholipids was critically evaluated by two different assay techniques, TLC densitometric scanning and a direct phosphate assay, developed recently at LTI. For both liposome preparations, flocculation appeared immediately after mixing the liposomes with the polymers. Precipitations occurred after several days of standing. The sediments, containing mainly liposomes, can easily be resuspended by gentle mixing. The dispersed solution appeared translucent white and did not resettle over a period of hours. Light microscopic observations showed the liposomes appeared in small aggregates of several microns in diameter. This tendency to aggregate did not change after as long as 4.5 months storage at various temperatures. No change of color was noted during the storage period, and all samples remained odorless. Slight pH drops were found in most of the samples, and these changes were temperature dependent.

The changes of pH are believed to be attributed to hydrolysis of polyvinylacetate, an impurity present in the polymers, rather than to the formation of free fatty acids as a result of lipid hydrolysis (see above). Values obtained by the TLC scanning techniques were generally lower than the numbers obtained by the direct phosphate assay. The pH 6.86 SUVs showed approximately 1.9, 6.7, and 12.7% lipid hydrolysis after 4.5 months of storage at 4°, 30°, and 38° C., respectively. A slower rate of hydrolysis was observed in the pH 6.7 SUVs.

B. Projected Level of Hydrolysis After 18 Months at Room Temperature

The Arrhenius Equation was applied to estimate the projected level of hydrolysis. Using the hydrolysis data obtained by the direct phosphate assay, rates of hydrolysis (K) at different temperatures (T) were calculated as follows:

$$K = \frac{H - H_o}{M}$$

Figure 6:
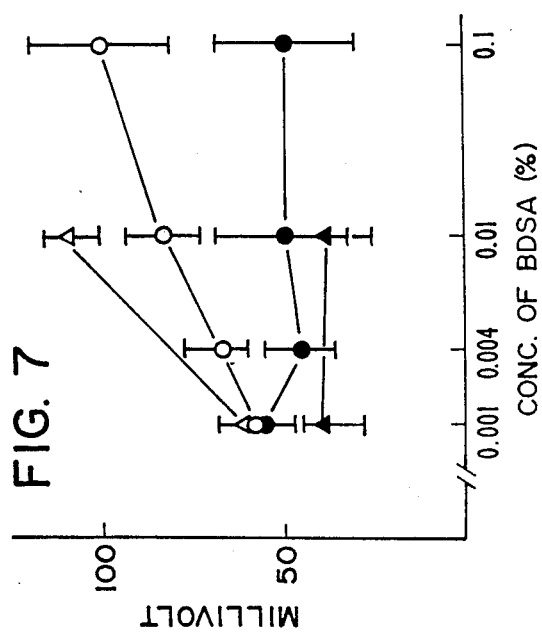
FIG. 6 is an Arrhenius plot of phospholipid hydrolysis in a liposome formulation at pH 6.8.

FIG. 6 present an Arrhenius plot of logarithm K (ln K) versus 1/T. The constant rate of hydrolysis for the phospholipids at 30° C. and pH 6.86 is estimated to be 1.2% per month. Assuming the same rate of hydrolysis throughout the shelf life period, 21.6% of hydrolysis could occur by the end of 18 months. Because hydrolysis appears to be exponential rather than a linear function (FIG. 5), the actual hydrolysis should be lower than this projected value.

EXAMPLE IX

Eye Irritancy Due to BDSA and BAC in SUVs

To determine an acceptable level of BDSA in a ophthalmic formulation, SUV suspensions containing obtaining BDSA at 0.01% and 0.05% were tested by the Draize rabbit eye irritancy test and an in vitro cytotoxicity study. A mouse model for acute corneal toxicity (Maurice) was also used to evaluate eye irritancy due to BDSA and BAC.

A. Draize Rabbit Eye Test.

Both liposome formulations containing 0.01% and 0.05% of BDSA were nonirritating to the rabbit eyes following a single topical application.

B. Cytotoxicity Study.

The agar overlay cytotoxicity assay was performed on the above liposome formulation containing 0.01% BDSA. Barnes-Hind comfort Tears ™ containing 0.01% benzalkonium chloride and 0.01% benzalkonium chloride solution were used as controls. Based on cytopathic changes such as crenation, vacuolization, nonuniformity of the cell monolayer and cytolysis, the two samples containing benzalkonium chloride were found to be more cytotoxic than the liposome formulation.

C. Corneal Permeability Test for Ocular Irritancy.

Four levels of BDSA, either in buffer solutions or formulated in the liposomes, were tested by the mouse irritancy model. The test measures the corneal permeability of a fluorescent dye, sulforhodamine, after administration of the test compound. The results of the test, expressed in observed ocular fluorescence as a function of BDSA concentration is shown in FIG. 7, where free BDSA is represented by open circles, and liposomal BDSA, by closed circles. As seen in the figure, increasing free BDSA from 0.001% to 0.1% progressively increased dye penetration, whereas with BDSA in the form of liposomes, there is no change in dye permeation. Similar results were found using 0.001% and 0.01% benzalkonium chloride (BAC), also plotted in FIG. 7, where open triangles represent free BAC and closed triangles, liposomal BAC.

EXAMPLE X

Eye Irritancy Related to Exposure Time

To evaluate the effect of the liposome exposure time on eye irritancy, one drop of the liposomes was instilled on one mouse eye 45 to 60 minutes prior to the dye application, in the above dye permeability test for ocular irritancy. Instillation of a drop of saline to the second eye was used as control. Fluorescent measurements from 6 mice showed no differences in dye permeation ($47\pm10$ mV vs. $51\pm17$ mV), supporting the study in Example IX which shows that ocular exposure to BDSA SUVs is non-irritating.

EXAMPLE XI

Optimal Liposome Dose

Figure 8:
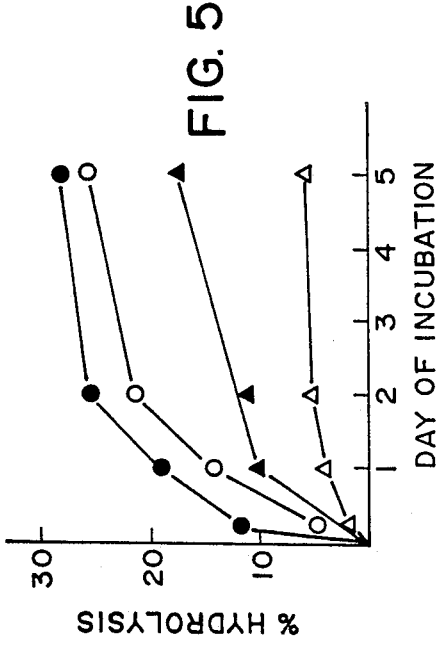
FIG. 8 shows the saturation of lipids in rabbit eyes following multiple instillation of liposomes.

To determine the ocular saturation level of liposomes in vivo, multiple doses of 10 $\mu$l BDSA SUVs, prepared as in Example II and labeled with $^{125}$I-lipids, were instilled in the rabbit eyes at one-hour intervals. Radioactivity remaining on the eye one hour after the instillation was determined by the scintillation probe technique. As shown in FIG. 8, retention of liposomes progressively increased following the repeated applications and became saturated after the fifth application. Because the average size of an eye drop is about 25 $\mu$l, it is possible that saturation may be attained by the application of $2\times25$ $\mu$l-size eye drops.

It is to be understood that while the invention has been described in conjunction with the preferred specific embodiments and uses, that various changes and modifications can be made without departing from the invention.

I claim:

1. A liposome composition for treating dry eye, comprising:
   (a) an aqueous medium buffered to a pH of between about 6.2 and 6.7;
   (b) dispersed in said aqueous medium, liposomes whose vesicle-forming lipids include about 60-90 mole percent saturated phosphatidylcholine; and
   (c) included in the lipid bilayers of said liposomes, 10-40 mole percent of a quaternary benzyl amine having an aliphatic hydrocarbon chain of between 15-20 carbon atoms.

2. The composition of claim 1, wherein the liposomes are predominantly in the size range between about 0.02-0.08 microns.

3. The composition of claim 1, wherein the liposomes and amine constitute between about 0.02-0.08 by weight of the composition.

4. The composition of claim 1, which further includes a high molecular weight polymer at a concentration which substantially increases the viscosity of the composition.

5. The composition of claim 4, wherein said polymer is selected from the group consisting of hydroxyethylcellulose, hydroxypropylcellulose, methylcellulose, polyvinylpyrrolidone, and polyvinylalcohol, and mixtures thereof.

6. The composition of claim 1, wherein the liposomes contain between about 1-10 mole percent vitamin A.

7. The composition of claim 1, which further includes the bacteriostatic agent benzalkonium chloride, at a concentration of between about 0.004% and about 0.01%.

8. The composition of claim 1, which further includes a calcium-ion chelator.

9. A liposome composition for treatment of dry eye, comprising:
   an aqueous medium buffered to a pH of about 6.2-6.7,
   dispersed in said aqueous medium, liposomes less than about 0.2 $\mu$m in diameter whose vesicle-forming lipids contain between about 10 and 30 mole percent benzyldimethylstearylammonium chloride and between about 70 and 90 mole percent saturated phosphatidyl choline;
   between about 0.02-0.06 percent by weight of a polymer selected from the group consisting of hydroxyethylcellulose, hydroxypropylcellulose, methylcellulose, polyvinylpyrrolidone, and polyvinylalcohol, and mixtures thereof, and
   a water-soluble calcium-ion chelating agent.

10. A liposome composition for treating dry eye, comprising:
    (a) an aqueous medium buffered to a pH of between about 6.2 and 6.7;
    (b) dispersed in said aqueous medium, liposomes whose vesicle-forming lipids include about 70-85 mole percent hydrogenated phosphatidylcholine; and
    (c) included in the lipid bilayers of said liposomes, 15-30 mole percent benzyldimethylstearylammonium chloride.

11. A method of treating dry eye, comprising
    providing an aqueous suspension of liposomes formulated to contain 60-90 mole percent saturated phosphatidylcholine and 10-40 mole percent of a quaternary benzyl amine having an aliphatic hydrocarbon chain of between 15-20 carbon atoms; and
    applying the suspension to an ocular surface in an amount sufficient to form an aqueous liposome matrix coating the surface.

12. The method of claim 11, wherein the liposome suspension is further formulated to contain benzalkonium chloride, at a concentration of between about 0.004% and about 0.01%.

13. A method of treating dry eye, comprising
    providing an aqueous suspension of liposomes formulated to contain between about 70-85 mole percent saturated phosphatidylcholine and between about 15-30 mole percent benzyldimethylstearylammonium chloride; and
    applying the suspension to an ocular surface in an amount sufficient to form an aqueous liposome matrix coating the surface.

* * * * *